(12) United States Patent
Chelius et al.

(10) Patent No.: US 7,138,521 B2
(45) Date of Patent: Nov. 21, 2006

(54) CRYSTALLINE OF N-[4-[2-(2-AMINO-4,7-DIHYDRO-4OXO-3H-PYRROLO[2,3-D]PYRIMIDIN-5-YL)ETHYL]BENZOYL]-L-GLUTAMIC ACID AND PROCESS THEREFOR

(75) Inventors: Erik Christopher Chelius, Innishannon (IE); Susan Marie Reutzel-Edens, Indianapolis, IN (US); Sharon Van den Berghe Snorek, Lafayette, IN (US)

(73) Assignee: Eli Lilly and Company, Indianapolis, IN (US)

( * ) Notice: Subject to any disclaimer, the term of this patent is extended or adjusted under 35 U.S.C. 154(b) by 693 days.

(21) Appl. No.: 10/182,991

(22) PCT Filed: Feb. 12, 2001

(86) PCT No.: PCT/US01/01229

§ 371 (c)(1),
(2), (4) Date: Nov. 20, 2002

(87) PCT Pub. No.: WO01/62760

PCT Pub. Date: Aug. 30, 2001

(65) Prior Publication Data

US 2003/0216416 A1    Nov. 20, 2003

(51) Int. Cl.
*C07D 487/04* (2006.01)
*A61K 31/505* (2006.01)

(52) U.S. Cl. ...................... 544/280; 514/258
(58) Field of Classification Search .............. 544/280; 514/258

See application file for complete search history.

(56) References Cited

U.S. PATENT DOCUMENTS

| 4,997,838 | A | | 3/1991 | Akimoto et al. |
| 5,106,974 | A | | 4/1992 | Akimoto et al. |
| 5,344,932 | A | | 9/1994 | Taylor |
| 5,416,211 | A | | 5/1995 | Barnett et al. |
| 6,013,828 | A | * | 1/2000 | Kjell et al. ............... 560/11 |

OTHER PUBLICATIONS

Brittain "Polymorphism in pharmaceutical solids" Marcel Dekker (1999) p. 2, 185.*
Evans R. C. "An introduction to crystal chemistry" Cambridge (1964) p. 284-285, 393-396.*
US Pharcopia #23, National formulary #18 (1995) p. 1843-1844.*
Cheronis N>D> "Semimicro experimental organic chemistry" (1958) p. 31-37.*
Kirk-Othmer Encyclop0edia of chemical technology, p. 1-7, ebook section crystallization (2005).*
Britten et al. "Activity of the multitargeted . . . " CA 131:67810 (1999).*
Calvert, AH; Walling, JM, "Clinical Studies with MTA," retrieved from STN, Database Accession No. 129:310246, Abstract XP-002160356.
Gangjee, et al., "Design, Synthesis, and X-ray crystal structure of a potent dual inhibitor of thymidylate synthase . . . ", J. Med. Chem., 2000, vol. 43, No. 21, 3837-3851.
Calvert, AH; Walling, JM, "Clinical studies with MTA", Br. J. Cancer, 1998, vol. 78, Supp. 3, 35-40.
Barnett, Charles J. et al: A Practical Synethesis of Multitargeted Antifolate LY231514, *Organic Process Research & Development*, vol. 3, pp. 184-188 (1999).

* cited by examiner

*Primary Examiner*—Celia Chang
(74) *Attorney, Agent, or Firm*—Elizabeth A. McGraw; Manisha A. Desai

(57) ABSTRACT

The invention relates to the field of pharmaceutical and organic chemistry and provides an improved process for preparing the novel heptahydrate crystalline salt of multi-targeted antifolate N-[4-[2-(2-amino-4,7-dihydro-4-oxo-3H-pyrrolo[2,3-d]-pyrimidin-5-yl)ethyl]benzoyl]-L-glutamic acid.

5 Claims, 1 Drawing Sheet

CRYSTALLINE OF N-[4-[2-(2-AMINO-4,7-DIHYDRO-4OXO-3H-PYRROLO[2,3-D]PYRIMIDIN-5-YL)ETHYL]BENZOYL]-L-GLUTAMIC ACID AND PROCESS THEREFOR

The present invention provides an improved crystalline form of the antifolate compound N-[4-[2-(2-amino-4,7-dihydro-4-oxo-3H-pyrrolo[2,3-d]pyrimidin-5-yl)ethyl]benzoyl]-L-glutamic acid, or pemetrexed disodium, also known as multitargeted antifolate or MTA (hereinafter pemetrexed), as well as the process for its preparation.

Pyrrolo[2,3-d]pyrimidine based antifolates have been used for a number of years as chemotherapeutic agents in the treatment of cancer. Pemetrexed is a 5-substituted pyrrolo[2,3-d]pyrimidine disodium salt. Extensive research and evaluation has revealed that pemetrexed is a potent inhibitor of several folate-requiring enzymes, including thymidine synthase, dihydrofolate reductase and glycinamide ribonucleotide formyltransferase. Pemetrexed disodium is currently in clinical trials for treatment of patients with a wide variety of solid tumors.

Surprisingly and unexpectedly, it has been found that pemetrexed can exist in the form of a heptahydrate which is much more stable than the previously known 2.5 hydrate. One method by which the heptahydrate is formed, is when the product is recrystallized from a volatile, water miscible solvent, such as acetone. The primary advantage of the heptahydrate crystalline form over the 2.5 hydrate crystal form is stability with respect to solvent content. The heptahydrate crystalline form is also more stable with respect to growth of related substances. These enhancements of stability make it easier to prepare the final formulation of the active pharmaceutical ingredient (API) and will extend the shelf-life of the API. Thus, the discovery of the present invention is that the heptahydrate crystalline form is what crystallizes from water/acetone. The key to isolating it is in how it is dried. When the heptahydrate is subjected to elevated temperatures, low humidity, and/or vacuum, it converts to the 2.5 hydrate crystal form by loss of water. A disadvantage of prior art water/ethanol procedure is that there are no known conditions that successfully remove ethanol or isopropyl alcohol from the wetcake without also losing water. The prior art water/ethanol procedure, as discussed by Barnett, et al., first produces the 7.0 ethanolate and then this is converted to the 2.5 hydrate upon evaporation of the ethanol. However, in the present invention, one is enabled to remove the volatile, water miscible solvent while preserving the original heptahydrate crystal form. This process has been demonstrated in the pilot plant, as described below.

U.S. Pat. Nos. 5,416,211, 5,344,932 and 5,539,113 disclose processes for preparing certain substituted pyrrolo[2,3-d]pyrimidine based antifolate derivatives, including pemetrexed. A number of pyrrolo[2,3-d]pyrimidine based antifolates, including pemetrexed, are described in U.S. Pat. Nos. 4,966,206; 5,106,974; 4,997,838; and 5,106,974.

The present invention provides a novel hydrate crystal form of disodium N-[4-[2-(2-amino-4,7-dihydro-4-oxo-3H-pyrrolo[2,3-d]-pyrimidin-5-yl)ethyl]benzoyl]-L-glutamic acid salt (hereinafter referred to as the "heptahydrate crystalline form"), having a characteristic X-ray diffraction pattern, which comprises the following intensity corresponding to d spacing: 7.78+/−0.04 Å when obtained at 22±2° C. and at ambient % relative humidity using a copper radiation source.

The invention further provides a method of use of the heptahydrate crystalline form for the manufacture of a medicament for the treatment of cancer.

The invention further provides for a process for preparing a medicament comprising combining the heptahydrate crystalline form in an aqueous solution.

The invention further provides for a formulation comprising the heptahydrate crystalline form in association with a pharmaceutically acceptable carrier.

The invention further provides for a process for the preparation of the heptahydrate crystalline form comprising crystallizing disodium N-[4-[2-(2-amino-4,7-dihydro-4-oxo-3H-pyrrolo[2,3-d]-pyrimidin-5-yl)ethyl]benzoyl]-L-glutamic acid salt from an appropriate solvent.

The invention further provides an article of manufacture comprising packaging material and a composition comprising the heptahydrate crystalline form contained within said packaging material, wherein said crystalline salt is effective in the treatment of cancer and a label which indicates that said crystalline salt can be used in the treatment of cancer.

The present invention further provides the heptahydrate crystalline salt of a compound of formula I:

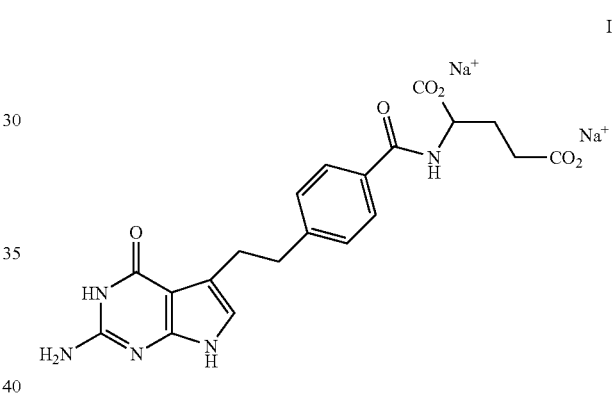

The present invention also provides a method for preparing such compounds by recrystallizing a compound of the formula I from a water miscible solvent.

Figure 1:
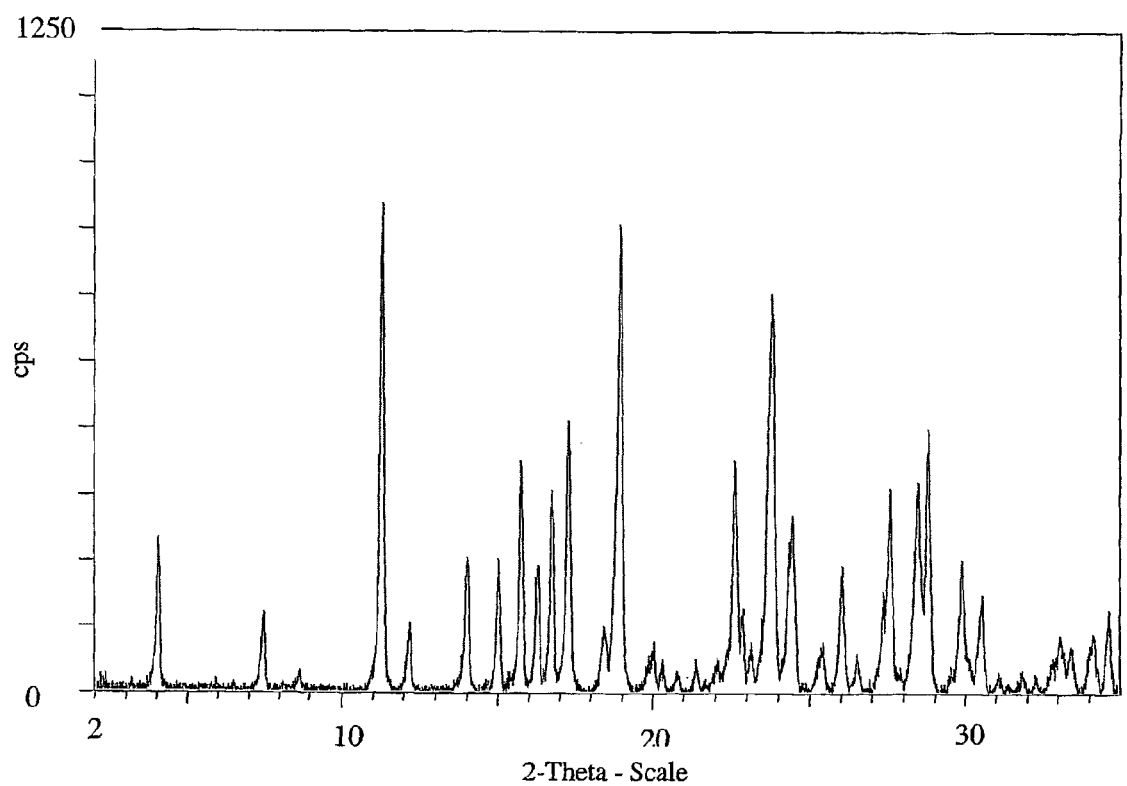
FIG. 1 is a representative XRD pattern for the heptahydrate crystalline salt taken at 25±2° C. and ambient relative humidity.

The compound of formula I can exist in tautomeric equilibrium with the corresponding 4(3H)-oxo compound. For illustrative purposes, the equilibrium for the pyrrolopyrimidine ring system and the numbering thereof, are shown below:

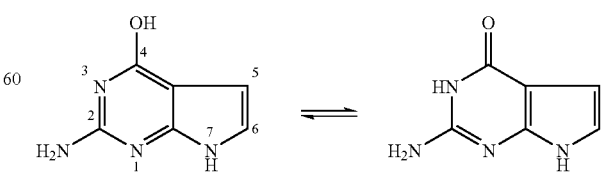

For convenience, the 4(3H)-oxo form is depicted in formula I, and the corresponding nomenclature is used throughout this specification. However, it is understood that such depictions include the corresponding tautomeric 4-hydroxy form.

Preferred process conditions to prepare the heptahydrate crystalline form of the present invention are as follows:

1. There is a critical interaction between equivalents of sodium hydroxide, temperature, and time during the saponification. This is due to a slow decomposition of pemetrexed in solution at high pH. The saponification should be held to less than 6 hours.
2. The pH of the crystallization of pemetrexed is between 2.5 and 3.5.
3. At least 5 volumes of water are used as a wash during the filtration to collect pemetrexed.
4. Between 2 and 3 equivalent of sodium hydroxide are used to form pemetrexed·2Na.
5. After the filtration, the aqueous solution of pemetrexed·2Na passes a qualitative test for extraneous materials.
6. The pH of the crystallization of pemetrexed·2Na is between 7 and 9.
7. At least 10 volumes of acetone are used as a wash during the filtration to collect pemetrexed·2Na.
8. Drying with humid nitrogen continues until acetone removal is complete. Completion is defined as either less than 100 ppm of acetone in the nitrogen that is exiting the drier, or validation of drying conditions.

Throughout this document, all temperatures are in degrees Celsius (° C.) and all expressions of proportion, percentage, and the like, are in weight units, except for solvents or mixtures thereof which are in volume units. The terms "ambient % relative humidity," as used herein, describes a relative humidity range from about 20% to about 80%. The following Examples further illustrate the present invention.

EXAMPLE 1

Preparation of the Heptahydrate Crystalline Form

N-[4-[2-(2-Amino-4,7-dihydro-4-oxo-3H-pyrrolo[2,3-d] pyrimidin-5-yl)ethyl]benzoyl]-L-glutamic acid diethyl ester p-toluenesulfonic acid salt and aqueous sodium hydroxide (4 to 6 equivalents) are combined and stirred at 0 to 30° C. The solution may be filtered. Water (to a total of between 10 and 16 volumes) and denatured ethanol (5 to 8 volumes) are added. Dilute hydrochloric acid and dilute sodium hydroxide solution (if needed) are added to adjust the pH to between 2.5 and 3.5. The slurry is warmed to between 60° C. and reflux (approximately 78° C.), then cooled to between 0 and 30° C. Pemetrexed is collected by filtration, and washed with water (not less than 2.5 volumes).

The pemetrexed wet cake, water (5 to 8 volumes), and sodium hydroxide (2 to 3 equivalents) are combined. The resulting solution is filtered. Dilute hydrochloric acid and dilute sodium hydroxide solution (if needed) are added to adjust the pH to between 7 and 9. The solution is heated to between 40 and 60° C. Acetone (22 to 36 volumes) is added. The mixture is cooled to between 0 and 30° C. The heptahydrate crystalline form is collected by filtration, washed with acetone (not less than 10 volumes), and dried under humid nitrogen at less than 50° C. Particle size or clumping may be reduced by milling or screening. Expected yield: greater than 80%

The Following Illustrates the Means of Making the Heptahydrate on a Larger Scale

| Materials | Name | Quantity | Kmoles |
|---|---|---|---|
| Compound IV | Pemetrexed Glutamate | 40 kg | .06 |
| 50% Sodium hydroxide solution | Sodium hydroxide solution 50% | 44.0 kg | .22 |
| Ethanol (Absolute-type 3A-denatured with 5% methanol) | Alcohol S.D. No. 3A absolute | 270 L | |
| Hydrochloric acid | Hydrochloric Acid | 19 kg | .19 |
| Deionized Water | Purified Water with Endotoxin control | 1515 L | |
| Acetone | Acetone | 1880 L | |

Purified water (265 L), 50% sodium hydroxide (22 kg, 4.5 equivalents), and N-[4-[2-(2-Amino-4,7-dihydro-4-oxo-3H-pyrrolo[2,3-d]pyrimidin-5-yl)ethyl]benzoyl]-L-glutamic acid diethyl ester p-toluenesulfonic acid salt (40 kg) were combined and stirred at between 20 and 30° C. until no solids were visible. The resulting solution was filtered. Purified water (270 L) and denatured ethanol (270 L) were added. The pH was adjusted to between 2.8 and 3.2 using dilute hydrochloric acid (106 L of 2N first, then 0.5 N HCl and/or 0.5N NaOH to hit the pH (63.8 kg of 0.5 N HCl and 5.34 kg of 0.5 N NaOH were required)). The slurry was adjusted to between 60 and 70° C., then cooled slowly to between 20 and 25° C. Pemetrexed was collected by filtration, and washed with purified water.

Pemetrexed, purified water (271 L), and 50% sodium hydroxide (10.2 kg) were combined at between 20 and 30° C. The pH was adjusted to between 7.5 and 8.5 using 0.5 N HCl (8.0 L were required). The resulting slurry was adjusted to between 45 and 55° C. and acetone (1300 L) was added. The mixture was cooled to between 20 and 25° C. Pemetrexed·2Na was collected by filtration, and washed with acetone. Residual acetone was removed at less than 35° C. using a stream of water-saturated nitrogen.

The Following Illustrates Preparation on a Small Scale

Into a 500 ml Erlenmeyer flask was placed 10.76 g (16.4 mmol) of N-[4-[2-(2-amino-4,7-dihydro-4-oxo-3H-pyrrolo [2,3-d]pyrimidin-5-yl)ethyl]benzoyl]-L-glutamic acid diethyl ester p-toluenesulfonic acid salt and 72 ml of 1 N NaOH. All of the solids dissolved in about 15 minutes. Deionized water (72 ml) and 3A EtOH (72 ml) were added. The pH of the mixture was adjusted to about 3 using dilute HCl. The slurry was heated to 65° C. and then allowed to cool to room temperature. The slurry was filtered and the wetcake was transferred to a 1 L Erlenmeyer. The wetcake was dissolved in 84 ml of 0.5 N NaOH and the pH adjusted to around 8 using dilute acid. The resulting solution was warmed to 45–50° C. and then 400 ml of acetone were added. Crystallization began after about 250 ml has been added. The slurry was cooled to room temperature and filtered. The solids were washed with acetone and dried in a vacuum oven at 25° C. under a slight vacuum (~700 mm Hg). A stream of damp air was passed through the oven during the 2 hour drying time. Yield=9.38 g (97%). Volatiles free potency: 92.3%. Total Related Subs.: 0.20%. Water: 21.2%. The theoretical water level for the heptahydrate crystalline form is 21.1%. Preferably, water should be present from about 19.5 to about 22.1%.

X-ray powder diffraction analysis can be readily performed as follows. After lightly grinding the sample with an agate mortar and pestle, the sample is loaded into a sample holder for the x-ray powder diffraction measurement. The x-ray powder diffraction patterns are measured using a Siemens D5000 x-ray powder diffractometer equipped with a CuKα source (α=1.54056 Å) operated at 50 kV and 40 mA using a Kevex solid-state silicon lithium detector. Interplanar spacings and peak intensities for the most prominent features were measured using a double-derivative peak picking method. Disodium MTA Hydrate Form I has a typical XRD pattern with interplanar spacings (d) in Angstroms and typical relative intensities ($I/I_o$) as shown in Tables I and II. The error of measurement is +/−0.04 Å. X-ray peaks with $I/I_o$ of 10% or greater were reported in the Tables below. The cutoff was chosen arbitrarily. The intensities are reported normalized to the most intense line. The effects of preferred orientation can be greatly reduced using a sample that is prepared in a manner that minimizes this effects, such as the use of a well ground sample.

TABLE I 2.5 Mole Hydrate Form
The 2.5 hydrate crystalline form is characterized by an X-ray diffraction pattern which comprises intensities corresponding to the following d spacings: 18.66 and/or 9.33 +/−0.04 Å when obtained at 22 ± 2° C. and at ambient % relative humidity using a copper radiation source. Preferably, a properly prepared sample of the 2.5 hydrate crystalline form may be characterized as having an X-ray diffraction pattern which comprises other strong, characteristic peaks corresponding to the following d spacings: 18.66, 9.33 and/or 4.92 +/− 0.04 Å when obtained at 22 ± 2° C. and 31 ± 10% relative humidity from a copper radiation source.

| d-spacing | I/Io | | |
|---|---|---|---|
| 18.66 | 100 | 4.66 | 22 |
| 11.38 | 18 | 4.59 | 16 |
| 9.33 | 69 | 4.26 | 12 |
| 8.71 | 11 | 3.87 | 52 |
| 8.44 | 24 | 3.80 | 12 |
| 6.22 | 28 | 3.72 | 38 |
| 5.92 | 17 | 3.43 | 19 |
| 5.69 | 55 | 3.29 | 25 |
| 5.59 | 10 | 3.13 | 10 |
| 5.14 | 11 | 3.11 | 16 |
| 4.92 | 49 | 3.08 | 18 |
| 4.75 | 24 | 2.95 | 11 |

7 Mole Hydrate Form
The heptahydrate crystalline form is characterized by an X-ray diffraction pattern which comprises intensities corresponding to the following d spacing: 7.78 +/− 0.04 Å when obtained at 22 ± 2° C. and at ambient % relative humidity using a copper radiation source. Preferably, a properly prepared sample of the heptahydrate crystalline form may be characterized as having an X-ray diffraction pattern which comprises other strong, characteristic peaks corresponding to the following d spacings: 21.60, 7.78, 5.26 and 3.22 +/− 0.04 Å when obtained at 22 ± 2° C. and 31 ± 10% relative humidity from a copper radiation source.

| d-spacing | I/Io | | |
|---|---|---|---|
| 21.60 | 34 | 3.83 | 10 |
| 11.71 | 15 | 3.72 | 69 |
| 7.78 | 100 | 3.62 | 31 |
| 7.22 | 15 | 3.41 | 24 |
| 6.29 | 31 | 3.24 | 14 |
| 5.86 | 21 | 3.22 | 36 |
| 5.60 | 44 | 3.12 | 38 |
| 5.42 | 34 | 3.09 | 47 |
| 5.26 | 37 | 2.97 | 26 |
| 5.10 | 43 | 2.97 | 21 |
| 4.79 | 10 | 2.91 | 19 |
| 4.66 | 84 | 2.91 | 16 |

-continued

7 Mole Hydrate Form
The heptahydrate crystalline form is characterized by an X-ray diffraction pattern which comprises intensities corresponding to the following d spacing: 7.78 +/− 0.04 Å when obtained at 22 ± 2° C. and at ambient % relative humidity using a copper radiation source. Preferably, a properly prepared sample of the heptahydrate crystalline form may be characterized as having an X-ray diffraction pattern which comprises other strong, characteristic peaks corresponding to the following d spacings: 21.60, 7.78, 5.26 and 3.22 +/− 0.04 Å when obtained at 22 ± 2° C. and 31 ± 10% relative humidity from a copper radiation source.

| d-spacing | I/Io | | |
|---|---|---|---|
| 3.91 | 44 | 2.69 | 11 |
| 3.87 | 14 | 2.67 | 11 |

Example 2

Stability Study Results for the 2.5 Hydrate Crystalline Form and the Heptahydrate Crystalline Form Several lots of the 2.5 hydrate crystalline form have been put on stability study. The results for water and total related substances are shown below. The solvents content in lots A, B and C includes water and ethanol. Water content in the 2.5 hydrate crystalline form is theoretically 8.7%; the ethanol content, however, is only 0.06%, 0.08%, and 0.1% respectively for these lots and is not a significant contribution to the total solvents. The solvents content for lot D is for water only. The ethanol level in lot D is 0.08%, and is not a significant contribution to the total solvents.

2.5 Hydrate Crystalline Form Results

The solvents (mainly water) content for all lots stored at 5° C. increases over time to approximately 21% which indicates the material is in the heptahydrate form. However, for lot C, only the last time point showed the material was in the heptahydrate form.

The accelerated conditions for lots A, B and C are 30° C., and for lot D is 25° C., 60% relative humidity. Only the D lot shows an increase in water content to the heptahydrate form. The other lots vary in water content over the time of the study.

The change in the percent total related substances for lots A, B and D which were stored at 5° C. did not change significantly over time. The percent total related substances for lot C did increase somewhat over time.

The change in the percent total related substances for lots A, B and C which were stored at accelerated conditions did change significantly over time. The percent total related substances for lot D did not increase somewhat over time.

Solvents Results (in Percent of Total) for the 2.5 Hydrate Crystalline Form Lots Stored at 5° C.

| time in months | Lot A | Lot B | Lot C | Lot D |
|---|---|---|---|---|
| 0 | 10.2 | 11.0 | 8.8 | 8.5 |
| 3 | 22.0 | 21.0 | 16.7 | 14.0 |
| 6 | 21.1 | 21.1 | 8.8 | 18.2 |
| 9 | N/A | N/A | N/A | 21.1 |
| 12 | 21.5 | 21.0 | 21.0 | 21.7 |
| 18 | 22.3 | | 20.8 | |
| 24 | 21.1 | | 20.4 | |

Solvents Results (in Percent of Total) for the 2.5 Hydrate Crystalline Form Lots Stored at Accelerated Conditions.

| time in months | Lot A | Lot B | Lot C | Lot D |
| --- | --- | --- | --- | --- |
| 0 | 10.2 | 11.0 | 8.8 | 8.5 |
| 1 | 10.9 | 15.5 | 20.6 | 14.0 |
| 2 | 10.6 | 12.9 | 19.3 | 20.5 |
| 3 | 10.7 | 11.5 | 17.2 | 20.8 |
| 6 | 9.3 | 11.2 | 8.9 | 21.2 |

Total Related Substances Results (in Percent of Total) for the 2.5 Hydrate Crystalline Form Lots Stored at 5° C.

| time in months | Lot A | Lot B | Lot C | Lot D |
| --- | --- | --- | --- | --- |
| 0 | 0.24 | 0.4 | 0.38 | 0.31 |
| 3 | 0.26 | 0.3 | 0.79 | 0.35 |
| 6 | 0.27 | 0.5 | 0.79 | 0.33 |
| 9 | N/A | N/A | N/A | 0.42 |
| 12 | 0.28 | 0.4 | 0.51 | 0.24 |
| 18 | 0.4 | | 0.43 | |
| 24 | 0.4 | | 0.44 | |

Total Related Substances Results (in Percent of Total) for the 2.5 Hydrate Crystalline Form Lots Stored at Accelerated Conditions.

| time in months | Lot A | Lot B | Lot C | Lot D |
| --- | --- | --- | --- | --- |
| 0 | 0.24 | 0.4 | 0.38 | 0.31 |
| 1 | 0.35 | 0.4 | 0.6 | 0.31 |
| 2 | 0.41 | 0.7 | 0.76 | 0.45 |
| 3 | 0.6 | 0.6 | 0.79 | 0.40 |
| 6 | 1.1 | 1.2 | 1.33 | 0.32 |

Heptahydrate Crystalline Form Results

The data for the 2.5 hydrate crystalline form give an indication that material that is in the heptahydrate form shows less degradation over time as compared to material that is not in the heptahydrate form. To test this hypothesis, a laboratory lot of the 2.5 hydrate crystalline form was converted to the heptahydrate form by placing the material in an 85% relative humidity chamber for 3 days. X-ray powder diffraction data was used to confirm that the material was in the heptahydrate form before the stability study was initiated. This material was put on a laboratory stability study and the results are shown below.

The water content for this lot stored at 5° C. is approximately 21%, which indicates the material is in the heptahydrate form. This value does not change significantly over time and indicates the heptahydrate material is stable with respect to water content at 5° C.

The accelerated conditions for this lot are 25° C./60% relative humidity and room temperature/uncontrolled humidity. The water content for material stored at these conditions is approximately 21%, which indicates the material is in the heptahydrate form. This value does not change significantly over time and indicates that the heptahydrate material is stable with respect to water content at both of these accelerated conditions.

The change in the percent total related substances for this lot, which was stored at 5° C. did not change significantly over time. This indicates that the heptahydrate material is stable and does not degrade significantly at 5° C.

The change in the percent total related substances for this lot, which was stored at accelerated conditions did not change significantly over time. This indicates that the heptahydrate material is stable even at the accelerated conditions and does not degrade significantly.

Solvents (Water) Results for the Heptahydrate Lot Stored at 5° C., 25° C./60% Relative Humidity, and 30° C./Uncontrolled Relative Humidity.

| Time | 5° C. | 25° C./60% RH | RT/uncontrolled RH |
| --- | --- | --- | --- |
| 0 | 21.0 | 21.0 | 21.0 |
| 0.25 | N/A | 21.1 | 21.3 |
| 0.5 | 21.0 | 21.1 | 20.8 |
| 0.75 | N/A | 20.1 | 20.6 |
| 1 | 20.6 | 20.1 | 20.6 |
| 2 | 21.1 | N/A | 21.1 |
| 3 | 21.3 | 20.7 | 21.1 |
| 6 | 21.1 | 21.3 | |
| 9 | 21.1 | N/A | |
| 12 | 21.9 | 21.7 | |

Total Related Substances Results for the Heptahydrate Lot Stored at 5° C., 25° C./60% Relative Humidity, and 30° C./Uncontrolled Relative Humidity.

| Time, mo. | 5 C. | 25 C./60% RH | RT/uncontrolled |
| --- | --- | --- | --- |
| 0 | 0.41 | 0.41 | 0.41 |
| 0.25 | N/A | 0.40 | 0.40 |
| 0.5 | 0.42 | 0.44 | 0.43 |
| 0.75 | N/A | 0.39 | 0.41 |
| 1 | 0.43 | 0.43 | 0.43 |
| 2 | 0.45 | N/A | 0.44 |
| 3 | 0.42 | 0.42 | 0.42 |
| 6 | 0.42 | 0.42 | |
| 9 | 0.40 | N/A | |
| 12 | 0.42 | 0.39 | |

The present invention also includes methods employing pharmaceutical formulations which contain, as the active ingredient, the heptahydrate crystalline form, in association with pharmaceutical carriers. A skilled artisan would know of such formulations and their manufacture, see, e.g., REMINGTON'S PHARMACEUTICAL SCIENCES, (16th ed. 1980).

The formulations are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The crystals are effective over a wide dosage range. For example, dosages per day normally fall within the range of about 0.5 to about 30 mg/kg of body weight. However, it will be understood that the amount of the crystal actually administered will be determined by a physician, in the light of the relevant circumstances, including the condition to be treated, the chosen route of administration, the actual crystal administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The crystals of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice.

In another embodiment, the present invention provides pharmaceutical compositions comprising a therapeutically effective amount of the crystal in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material, which can serve as a vehicle or medium for the active-ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The crystals of the present invention may be administered orally, for example, with an inert diluent or with an edible carrier. They may be enclosed in gelatin capsules or compressed into tablets. For the purpose of oral therapeutic administration, the crystals may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the crystal present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials, which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the crystals of the present invention may be incorporated into a solution or suspension. These preparations should contain at least 0.1% of a crystal of the invention, but may be varied to be between 0.1 and about 50% of the weight thereof. The amount of the heptahydrate crystalline form present in such compositions is such that a suitable dosage will be obtained. Preferred compositions and preparations are able to be determined by one skilled in the art.

The crystals of the present invention may also be administered by inhalation, such as by aerosol or dry powder. Delivery may be by a liquefied or compressed gas or by a suitable pump system, which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The crystals of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, such as sodium chloride and mannitol, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials mane of glass or plastic.

The following formulation example is illustrative only and is not intended to limit the scope of the invention in any way. "Active ingredient" means the heptahydrate crystalline form.

EXAMPLE 1

| active ingredient | 4% (total solution) |
| --- | --- |
| L-cysteine | 0.03% (total solution) |
| a pharmaceutically acceptable excipient | water |

The pH of the solution was adjusted to 8.5 using sodium hydroxide. The pH adjusted solution was protected from light. The solution was purged with nitrogen for twenty minutes and then sterile filtered. The formulation was dispensed into prewashed, depyrogenated vials and then stoppered with a prewashed, presterilized teflon coated stopper.

Caps were attached using a crimper. The sterile filtration and dispensing steps were conducted using a nitrogen isolator (5% v/v Oxygen).

The solution filled vials were heat sterlized.

We claim:

1. A heptahydrate crystal form of disodium N-[4-[2-(2-amino-4,7-dihydro-4-oxo-3H-pyrrolo[2,3-d]-pyrimidin-5-yl)ethyl]benzoyl]-L-glutamic acid salt, having an X-ray diffraction pattern, which comprises the following peaks corresponding to d spacing: 7.78±0.04 Å when obtained at 22±2° C. and ambient % relative humidity from a copper radiation source.

2. A process for preparing a composition of disodium N-[4-[2-(2-amino-4,7-dihydro-4-oxo-3H-pyrrolo [2,3-d]pyrimidin-5-yl)ethyl]benzoylJ-L-glutamate comprising combining the hepthydrate crystalline form of claim 1 with a buffer in an aqueous solution.

3. A process for the preparation of a pharmaceutical formulation of disodium N-[4-[2-(2-amino-4,7-dihydro-4-oxo-3H-pyrrolo[2,3-d]pyrimidin-5-yl)ethyl]benzoyl]-L-glutamate, which comprises bringing disodium N-[4-[2-(2-amino-4,7-dihydro-4-oxo-3H-pyrrolo[2,3-d]pyrimidin-5-yl)ethyl]benzoyl]-L-glutamate heptahydrate into association with a pharmaceutically acceptable carrier.

4. A process for preparing the heptahydrate of claim 1, which comprises crystallizing disodium N-[4-[2-(2-amino-4,7-dihydro-4-oxo-3H-pyrrolo[2,3-d]-pyrimidin-5-yl)ethyl]benzoyl]-L-glutamic acid salt from a solution comprising disodium N-[4-[2-(2-amino-4,7-dihydro-4-oxo-3H-pyrrolo[2,3-d]-pyrimidin-5-yl)ethyl]benzoyl]-L-glutamic acid, water, and a water miscible solvent; and drying the crystalline disodium N-[4-[2-(2-amino-4,7-dihydro-4-oxo-3H-pyrrolo[2,3-d]-pyrimidin-5-yl)ethyl]benzoyl]-L-glutamic acid salt with humid nitrogen.

5. The process of claim 4, wherein the solvent is acetone.

* * * * *

UNITED STATES PATENT AND TRADEMARK OFFICE
CERTIFICATE OF CORRECTION

PATENT NO. : 7,138,521 B2 Page 1 of 1
APPLICATION NO. : 10/182991
DATED : November 21, 2006
INVENTOR(S) : Erik Christopher Chelius et al.

It is certified that error appears in the above-identified patent and that said Letters Patent is hereby corrected as shown below:

Title page, column 1, after
(65)    Prior Publication Data
        US 2003/0216416 A1     Nov. 20, 2003:

Insert --Related U.S. Application Data
(60) Provisional application No. 60/184,964     February 25, 2000.--

Signed and Sealed this

Ninth Day of November, 2010

David J. Kappos
*Director of the United States Patent and Trademark Office*